(12) United States Patent
Caers et al.

(10) Patent No.: US 6,274,756 B1
(45) Date of Patent: Aug. 14, 2001

(54) ESTERS, ETHERS, AND COMPOSITIONS COMPRISING THEM

(75) Inventors: Raphael Frans Ivo Caers, Edegem (BE); Richard Henry Schlosberg, Bridgewater, NJ (US)

(73) Assignee: Exxon Chemicals Patents, Inc., Houston, TX (US)

( * ) Notice: Subject to any disclaimer, the term of this patent is extended or adjusted under 35 U.S.C. 154(b) by 0 days.

(21) Appl. No.: 09/230,089
(22) PCT Filed: Jul. 17, 1997
(86) PCT No.: PCT/GB97/01913
  § 371 Date: Jun. 21, 1999
  § 102(e) Date: Jun. 21, 1999
(87) PCT Pub. No.: WO98/03462
  PCT Pub. Date: Jan. 29, 1999

(30) Foreign Application Priority Data

Jul. 18, 1996 (GB) .................................................. 9615089

(51) Int. Cl.$^7$ .................................................. C07C 69/76
(52) U.S. Cl. ............................ 560/76; 560/190; 560/205; 524/296
(58) Field of Search ............................ 524/296; 560/76, 560/190, 205

(56) References Cited

U.S. PATENT DOCUMENTS

| | | | |
|---|---|---|---|
| 3,619,234 | * 11/1971 | Weihsbach | 117/33.5 |
| 4,504,410 | * 3/1985 | Hempel | 252/358 |
| 4,952,401 | * 8/1990 | Hobbs | 424/405 |
| 5,503,755 | * 4/1996 | Danner | 252/8.6 |
| 5,529,973 | * 6/1996 | Shinohara | 503/227 |
| 5,783,618 | * 7/1998 | Danner | 524/275 |
| 5,908,951 | * 6/1999 | Kobayashi | 556/479 |

FOREIGN PATENT DOCUMENTS

| | | |
|---|---|---|
| 9622268 | * 7/1996 | (WO) . |
| WO 96/22268 | 7/1996 | (WO) . |

OTHER PUBLICATIONS

A.M. Koganovskii et al., "Kinetics of the ion exchange absorption of tetramethyloctanebenzene sulfonate ions and micelles by the resin", Chemical Abstracts, vol. 68, No. 4, pp. 1585, Abstract No. 16449t, Jan. 22, 1968, Columbus, Ohio, US.

John A. Findlay et al, "Novel sulfated hydrocarbons from the sea cucumber *Cucumaria frondosa*", Chemical Abstracts, vol. 114, No. 17, p. 475, Abstract No. 161142k, Apr. 29, 1991, Columbus, Ohio, US.

John A. Findlay et al, "Novel Sulfated Hydrocarbons From the Sea Cucumber *Cucumaria Fondosa*", Journal of Natural Products, vol. 54, No. 1, pp. 302–304, Jan.–Feb., 1991.

* cited by examiner

Primary Examiner—Paul R. Michl

(57) ABSTRACT

Esters and ethers of 2,4,6-trimethylnonanol, compositions comprising them, their uses, and processes for their manufacture.

26 Claims, No Drawings

ESTERS, ETHERS, AND COMPOSITIONS COMPRISING THEM

CROSS-REFERENCE TO RELATED APPLICATIONS

The present application is a U.S. National Stage Patent Application of PCT application PCT/GB97/01913, filed Jul. 17, 1997, which claims priority to Great Britain application GB 9615089.1, filed Jul. 18, 1996. The present application is also a continuation in part of U.S. application Ser. No. 08/860,638, filed in the U.S.P.T.O. on Jul. 17, 1997, which is the National Stage Application of PCT Application PCT/EP96/00267, filed on Jan. 17, 1996, which claims priority to European Patent application EP 95300301.9, filed on Jan. 18,1996.

This invention relates to esters and ethers of certain alcohols, to their uses, and to compositions comprising them. More especially, the invention relates to the use of the compounds as surfactants, synthetic lubricants or lubricant components and as plasticizers, to polymeric compositions plasticized by the esters, and to products made from the compositions. Certain of the compounds are novel.

The esters of 2-ethylhexanol, especially the phthalate, are among the most commonly used plasticizers. The alcohol is obtainable by, for example, subjecting propene to hydroformylation, dimerizing the resulting butanal by the aldol reaction, a term which is used throughout this specification, including the claims, as including the subsequent dehydration to an unsaturated aldehyde, and hydrogenating the resulting aldehyde to form a saturated alcohol.

The propene, produced for example by a steam cracking plant, has to be purified before hydroformylation, and its cost as feedstock is increased as a result.

Although the plasticizer esters derived from 2-ethylhexanol are widely used, for some purposes, for example where a lower volatility, or a stronger solvator for the polymer is needed, higher molecular weight esters, for example those based on $C_9$ to $C_{12}$ alcohols, are preferred. The $C_9$ esters presently available commercially are typically derived from an isomeric mixture of $C_9$ alcohols and the users' requirements for product consistency may result in manufacturing complexities.

These complexities result from variations in feed composition and reaction conditions in the process for the manufacture of the precursors to the alcohols. These precursors may be formed for example by oligomerizing a mixed $C_3$ to $C_5$ olefin feed, giving a mixture of linear and branched olefins, predominantly having six to ten carbon atoms, from which is distilled a mixed $C_8$ olefin, which is in turn hydroformylated (oxonated) and hydrogenated to form the isomeric $C_9$ alcohol mixture.

In other commercial processes, the $C_9$ alcohol precursors are typically obtained by dimerizing butene streams and oxonating the resulting $C_8$ olefin fraction. The butene stream itself contains a mixture of isomers, in proportions that may vary over a period, and the cobalt oxo process causes some isomerization. Thus the alcohols resulting from hydrogenation of the aldehyde form a reaction product of variable isomer distribution together with lower and higher homologues, necessitating further treatment if customers's product specifications are to be met. The processes for making other higher alcohols differ from those used in $C_9$ alcohol production but generally result in isomeric mixtures.

In a typical commercial process for the manufacture of a plasticizer ester, the alcohol is employed in excess over the acid, and alcohol is stripped from the ester product and recycled. Because of the recycling, less reactive isomers tend to become more concentrated in the reaction vessel as the reaction progresses, resulting in a change in the composition over time. In turn, the downstream users's quality control inspection of the incoming product is more onerous than if it were a single isomer.

Processing of thermoplastics containing a multi-isomer plasticizer may be more difficult to control in certain applications, resulting in a greater possibility of inconsistencies in properties between different batches of the final product.

This in turn may require the user to have tighter control over process variables, e.g., oven temperature ranges in motor vehicle paintshops and flooring material lines, than would otherwise be necessary, and also complicates material recycling.

Finally, effluent and environmental monitoring is more difficult; e.g., a single isomer material may have a minimum detectability an order of magnitude lower than a multi-isomer material.

There accordingly remains a need for an alternative route to commercially useful organic molecules, and more especially one that provides flexibility and a greater control of product structure, particularly the ability to produce single isomers if desired. There also remains a need for esters and ethers having enhanced properties for various uses.

The present invention provides an ester or an ether of 2,4,6-trimethylnonanol.

The present invention also provides a process for the manufacture of 2,4,6-trimethylnonanol, which comprises subjecting 2,4-dimethylheptanal to aldol condensation with propanal, and hydrogenating the resulting unsaturated aldehyde to the desired $C_{12}$ alcohol.

The present invention further provides a process for the manufacture of a saturated aliphatic $C_{12}$ alcohol or an ester thereof which comprises subjecting a $C_6$ aldehyde to an aldol condensation with propanal to form an unsaturated $C_9$ aldehyde and hydrogenating the $C_9$ aldehyde (a) to form a saturated $C_9$ aldehyde, which is subjected to an aldol condensation with propanal to form a $C_{12}$ unsaturated aldehyde, which $C_{12}$ unsaturated aldehyde is hydrogenated (b) to form a saturated $C_{12}$ alcohol and, optionally, (c) esterifying the $C_{12}$ alcohol.

The starting $C_6$ aldehyde is advantageously 2-methylpentanal, the resulting $C_9$ and $C_{12}$ aldehydes being the unsaturated and saturated 2,4-dimethylhept(en)- and (an)als, and 2,4,6-trimethylnon(en)- and (an)als.

If desired, part of the unsaturated $C_9$ aldehyde may be hydrogenated to a saturated $C_9$ alcohol, which may also be esterified, either together with the $C_{12}$ alcohol or separately.

Formation of a saturated alcohol may be carried out in two stages through a saturated aldehyde or in a single stage to the saturated alcohol, in which process the saturated aldehyde is typically formed as an intermediate and not isolated.

The esters and ethers of the invention, or produced by the process of the invention, are suitable for use as solvents, paint coalescers, plasticizers, adhesives, surfactants, viscosity index improvers, synthetic lubricants, flame retardants, lubricant components, anti-wear agents, hydraulic fluids, cetane improvers, drilling fluids, thermoplastic and textile processing aids, polymer, especially vinyl chloride polymer, stabilizers, polymerizable monomers and fragrances.

The acid of the ester may be inorganic or organic; if the latter, a carboxylic acid is preferred. Among organic acids, aromatic acids are preferred for plasticizer manufacture, although aliphatic acids are also employed. As examples of acids, acetic, propionic, valeric, isovaleric, n-heptanoic, n-octanoic, n-decanoic, neodecanoic, lauric, stearic, isostearic, oleic, erucic, succinic, phthalic (1,2-benzenedicarboxylic), isophthalic, terephthalic, adipic, fumaric, azelaic, 2-methylpentanoic, 2,4-dimethylheptanoic, 2,4,6-trimethylnonanoic, sebacic, trimellitic, pyromellitic, acrylic, methacrylic, tall oil, naphthenic and naphthalene-type acids, carbonic, nitric, sulphuric, phosphoric and phosphorous and their thio-analogous, acids and $C_6$ to $C_{13}$ oxo and neo acids generally may be mentioned. The esters of the $C_9$ and especially the $C_{12}$ alcohols with oxo and neo acids have especial utility as drilling fluids and power transmission fluids. The phosphate esters have especial utility as flame retardants while the phosphite esters provide vinyl chloride polymer stabilizers.

Esters with monobasic and dibasic acids are preferred for lubricants and lubricant components; advantageously the resulting esters contain from 15 to 40 carbon atoms; adipates, azelates, and phthalates are especially preferred for lubricant manufacture. The esters with unsaturated carboxylic acids, e.g., with acrylic and methacrylic acid, provide polymerizable monomers, suitable as sole or co-monomer in thermoplastics manufacture, or in polymers used in or as adhesives, VI improvers, and coating resins.

The invention accordingly also especially provides an ester of 2,4,6-trimethylnonanol with a polybasic acid, especially an ester with a dibasic acid. The invention also provides an ester of a polybasic acid in which all the acid groups are esterified by 2,4,6-trimethylnonanol, especially a dibasic acid both acid groups of which are thereby esterified. Among specific esters provided by the invention there may be mentioned, for example, 2,4,6-trimethylnonyl acetate, the bis(2,4,6-trimethylnonyl) esters of 1,2-benzenedicarboxylic and hexanedioic acids and the tris esters of 1,2,4-benzenetricarboxylic acid, the latter providing a plasticized polymer with good electrical properties. In vinyl chloride polymer compositions, the plasticizer, especially phthalate, $C_{12}$ ester, acts as a softening aid for the polymer, a plasticized polymer (e.g. pvc) of a given hardness containing less polymer than comparable plasticized materials, prepared with other $C_{12}$ phthalate esters, thereby giving the esters of the invention an economic advantage as a result of the resulting volume cost advantage. The $C_{12}$ phthalate ester also has advantages in the manufacture of automotive sealant compositions in part because of the increased viscosity and enhanced viscosity stability of the compositions.

The $C_{12}$ phthalate ester has a lower volatility than presently employed low volatility plasticizers, e.g., diisodecyl phthalate. The $C_{12}$ adipate correspondingly has a lower volatility than the presently employed commercial lubricant diisodecyl adipate, and the $C_{12}$ acetate has a lower volatility than the commercially available isodecyl acetate solvent.

Both esters and ethers provide surfactants, for use, for example, in detergents, emulsifiers, and demulsifiers. As specific examples there may more especially be mentioned the following derivatives of 2,4,6-trimethylnonanol, ROH:

sulphates, $ROSO_3H$, and their salts, especially sodium;
sulphonates, $RSO_3H$, and their salts, especially sodium;
alkoxy sulphonates, otherwise known as ether-sulphates, for example $RO(R^2O)_nSO_3H$, wherein $R^2O$ represents ethoxy (EO) or propoxy (PO) and n advantageously represents from 1 to 30, preferably from 1 to 4, and their salts, especially sodium;
alkoxylates, for example, those containing EO, or PO, or both groups, for example, polyethyleneglycol ethers $RO(EO)_mH$ with m being, for example, from 3 to 100, more especially from 3 to 15, or poly-polyglycol ethers, $RO(EO)_p(PO)_qH$ or $RO(PO)_q(EO)_pH$ wherein p advantageously represents from 3 to 6 and q advantageously independently represents from 3 to 6; and etheramines, for example, oxyalkylene wherein $R^3$, $R^4$ and $R^5$ each independently represent an alkylene group, advantageously ethylene or propylene, amines, for example the example compounds of the formula $ROR^3NH_2$ or $ROR^4NHR^5NH_2$ for example the oxypropylene amine $RO(CH_2)_3NH_2$, diamine $RO(CH_2)_2NH(CH_2)_2NH_2$, and the nitriles (—C≡N), alkoxylates (e.g.,—N($C_2H_4OH)_2$ or —N($C_3H_6OH)_2$ or quaternary ammonium salts, for example, —N(EO or $PO)_2CH_3]^+X^-$, where X may represent, for example, chlorine, of the mono- or diamines.

The glycidyl ether,

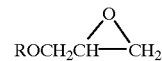

has utility in the manufacture of coating resins.

The invention accordingly also provides an ether of 2,4,6-trimethylnonanol, especially a hydroxy or amino ether, more especially an polyoxyalkylene hydroxy- or amino-ether, or a derivative thereof. The ethers according to the invention may be made by methods known per se, for example as practised in the art or described in the literature.

Specific examples of esters in accordance with the invention and their applications include the esters of 2,4,6-trimethylnonanol with acetic (solvent), acrylic and methacrylic (polymerizable monomer), phthalic, adipic, sebacic, trimellitic and pyromellitic acids (plasticizer, lubricant or lubricant component for, e.g., engine oil, hydraulic fluid, refrigerant oil for hydrofluorocarbon refrigerants, fuel additive for mogas and diesel fuels). The polycarboxylic acids may be completely esterified by 2,4,6-trimethylnonanol (the $C_{12}$ alcohol), which is preferred for some applications, or may be partly esterified by the $C_{12}$ alcohol and partly by other alcohols, especially 2,4-dimethylheptanol and/or 2-methylpentanol.

In an embodiment of the invention especially useful as lubricant or lubricant component, there is provided a mixed ester of the $C_9$ or the $C_{12}$ alcohol if desired also in admixture with 2-methylpentanol, a polycarboxylic acid, e.g., one of those mentioned above, and a polyhydric alcohol, the ester also optionally being derivable from a monocarboxylic acid, e.g., one of those mentioned above. As polyhydric alcohol, there may be mentioned, more especially, one having at most six hydroxyl groups. Aliphatic alcohols are preferred, especially those with some degree of steric hindrance, examples being neopentyl glycol, pentaerythritol, dipentaerythritol, tripentaerythritol, trimethylol -ethane, -propane, and -butane, 2-ethyl-2-methyl- and 2,2,-diethyl-1,3-propanediol and 2,2,4,-trimethylpentane-1,3-diol. Other preferred polyols are 2,2-dimethylol butane, ethylene glycol, propylene glycol, 1,4-butanediol, sorbitol, inositol, and polyalkylene glycols (e.g., poly-ethylene, -propylene or -butylene glycol, blends thereof or copolymerized mixtures of the monomeric compounds). Other, somewhat less preferred, examples are polyoxyalkylene glycols, other 2-substituted propanediols, and other substituted or unsubstituted butanediols, pentanediols, hexanediols, heptanediols and octanediols.

The invention also provides a dihydrocarbyl dithiophosphoric acid, and a metal or ammonium dihydrocarbyl dithiophosphate, in which at least one of the hydrocarbyl groups is a 2,4-dimethylheptyl or a 2,4,6-trimethylnonyl group. Advantageously both hydrocarbyl groups are the specified $C_9$ or $C_{12}$ alkyl groups. Advantageously, the metal is zinc. The DDPA's and DDP's are made by methods known Per se.

The invention also provides a plasticizer composition comprising the ester of a polybasic acid and an alkanol blend comprising a major proportion of 2,4,6-trimethylnonanol and a minor proportion (up to 50%) of another alkanol or alkanols having from 6 to 12 carbon atoms, the alkanols having 6 to 12 carbon atoms including, for example, 2-methylpentanol and 2,4-dimethylheptanol. The other alkanols may be linear or branched, or mixtures thereof.

If an aldehyde other than propanal is also present in the aldol reaction mixture, then a mixture of aldol products will be formed having a range of carbon atom numbers, as a result of cross-aldolization. The invention accordingly also provides the esters obtained by reaction of the resulting alcohol mixture with an acid. It will be appreciated that, where the acid is polybasic, mixed esters will be present.

The invention further provides a composition comprising a plasticizer ester, or plasticizer composition, according to the invention and a polymer plasticized thereby. The invention also provides a shaped structure formed of the plasticized polymer. Advantageously, the ester is made by a process in accordance with the invention.

The $C_6$ and $C_9$ aldehydes required as starting materials for various aspects of the process according to the invention may be obtained as described in detail in WO 96/22268, the disclosure of which is incorporated by reference herein. That specification also contains a general description of the aldol process.

The esters may be produced by methods known per se or described in the literature from the alcohol and the relevant acid or, preferably, where appropriate, the anhydride, optionally in the presence of a solvent. Elevated temperatures and reduced pressures are generally employed to drive the reaction toward completion by removal of the water produced. Catalysts may be employed. Suitable catalysts include, for example, a titanium catalyst e.g., a tetraalkyl titanate, especially tetra-iso-propyl or tetraoctyl ortho titanate, or a sulphonic acid, e.g., p-toluene sulphonic acid or methylsulphonic acid. Any catalyst present in the reaction product may be removed by alkali treatment and water washing. Advantageously, the alcohol is used in slight, e.g., from 10 to 25%, molar excess relative to the number of acid groups in the acid.

The esters of the invention may be used as a plasticizer for numerous polymers, for example, cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated carboxylic acids e.g., methacrylates, and/or olefins; nitrile rubbers; and post-chlorinated vinyl chloride polymers. Poly(vinyl chloride) is of especial interest. The proportion of plasticizer may vary within wide limits, but is generally 10 to 200 parts by weight per 100 parts of polymer, more especially 20 to 100 parts per 100.

The esters of the invention may be used alone as plasticizer, or in admixture with one another, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, or butyl benzyl phthalate, or mixtures thereof. They may also or instead be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. For example, they may be in the form of a dryblend, a paste, or a plastisol, depending on the grade of the resin employed. They may be used, for example, as coatings, in dipping, spraying, injection or rotational moulding, extrusion, or as self-supporting films and sheets, and may readily be foamed. End uses include flooring materials, wall coverings, moulded products, upholstery materials, leather substitutes, electrical insulation, especially wire and cable, coated fabrics, toys, and automobile parts.

The invention also provides a composition comprising an ester of the invention and a refrigerant, especially a fluorocarbon refrigerant, and more especially HFC 32 (difluoromethane) or HFC 134a (1,1,1,2-tetrafluoroethane). More especially, the invention provides such a composition also comprising at least one of a hydrolytic stability enhancer, e.g., a hindered phenol or an aromatic amine, an antioxidant, corrosion inhibitor, and a metal deactivator.

We claim:

1. An ester of 2,4,6trimethylnonanol other than 2,4, 6trimethylnonane-1 sodium sulfate.

2. An ester as claimed in claim 1, wherein said ester is derived from an inorganic acid.

3. An ester as claimed in claim 1, wherein said ester is derived from an organic acid.

4. An ester as claimed in claim 3, wherein the organic acid is a monocarboxylic acid.

5. An ester as claimed in claim 4, wherein the organic acid is acetic, acrylic, or methacrylic acid.

6. An ester as claimed in claim 3, wherein the organic acid is a polycarboxylic acid.

7. An ester as claimed in claim 6, wherein the organic acid is phthalic, adipic, or trimellitic acid.

8. An ester as claimed in claim 6, wherein each carboxyl group of the organic acid is esterified by said 2,4,6-trimethylnonanol.

9. A complex ester of a carboxylic acid containing at least two carboxyl groups, a polyol, and an alcohol selected from the group consisting of 2,4,6-trimethylnonanol and 2,4-dimethylheptanol.

10. An ester as claimed in claim 9, wherein the polyol is neopentyl glycol, pentaerythritol, dipentaerythritol, trimethylolethane, or trimethylolpropane.

11. A plasticizer composition comprising an ester as claimed in claim 7.

12. A plasticized polymeric composition comprising a thermoplastic polymer and an ester or plasticizer composition as claimed in claim 7.

13. A composition comprising a refrigerant and an ester as claimed claim 3 or claim 9.

14. A composition as claimed in claim 13, wherein the refrigerant is a fluorocarbon refrigerant.

15. A composition as claimed in claim 14, which comprises HFC 32 or HFC 134a.

16. A composition as claimed in claim 13, which further comprises a compound selected from the group consisting of a hydrolytic stability enhancer, an antioxidant, corrosion inhibitor, and a metal deactivator, and combinations thereof.

17. A dihydrocarbyl dithiophosphoric acid in which at least one of the hydrocarbyl groups is a 2,4-dimethylheptyl or a 2,4,6-trimethylnonyl group.

18. A metal dihydrocarbyl dithiophosphate in which at least one of the hydrocarbyl groups is a 2,4-dimethylheptyl or a 2,4,6-trimethylnonyl group.

19. An ammonium dihydrocarbyl dithiophospate acid in which at least one of the hydrocarbyl groups is a 2,4-dimethylheptyl or a 2,4,6-trimethyinonyl group.

20. A process for the manufacture of 2,4,6-trimethylnonanol, which comprises subjecting 2,4-dimethylheptanal to aldol condensation with propanal, and hydrogenating the resulting unsaturated aldehyde to the desired $C_{12}$ alcohol.

21. A process as claimed in claim 20, wherein the desired $C_{12}$ alcohol is esterified.

22. A compound of the formula $RO(R^2O)_nOSO_3H$, wherein R is 2,4,6-trimethyinonanyl, $R^2O$ is ethoxy (EO) or propoxy (PO) and n is from 0 to 4.

23. A salt of a compound as claimed in claim 22, other than 2,4,6-trimethyinonane-1-sodium sulphate.

24. An ether of 2,4,6-trimethylnonanol.

25. A compound of the formula $RO(R^2O)_mH$, wherein R is 2,4,6-trimethylnonanyl, and $R^2O$ is ethoxy (EO) or propoxy (PO) and m is from 3 to 15.

26. A compound of the formula $RO(EO)_p(PO)_qH$, wherein R is 2,4,6-trimethylnonanyl, EO is ethoxy and PO is propoxy and p and q independently are from 3 to 6.

* * * * *